United States Patent
Matsumoto et al.

(10) Patent No.: US 6,850,597 B2
(45) Date of Patent: Feb. 1, 2005

(54) X-RAY IMAGE PHOTOGRAPHING APPARATUS AND GRID DEVICE

(75) Inventors: Kazuhiro Matsumoto, Tochigi (JP); Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 155 days.

(21) Appl. No.: 10/061,292

(22) Filed: Feb. 4, 2002

(65) Prior Publication Data

US 2002/0126800 A1 Sep. 12, 2002

Related U.S. Application Data

(63) Continuation-in-part of application No. 09/392,617, filed on Sep. 9, 1999, now Pat. No. 6,501,829.

(30) Foreign Application Priority Data

Sep. 11, 1998 (JP) .......................................... 10-276484

(51) Int. Cl.$^7$ ............................................... G21K 1/00
(52) U.S. Cl. ........................ 378/154; 378/155; 378/186
(58) Field of Search ................................ 378/154, 155, 378/98.8, 186, 207

(56) References Cited

U.S. PATENT DOCUMENTS

| 5,661,818 A | 8/1997 | Gaborski et al. ........... 382/132 |
|---|---|---|
| 5,809,107 A | 9/1998 | Schmitt ....................... 378/154 |
| 6,244,507 B1 * | 6/2001 | Garland et al. ............. 235/383 |
| 6,501,829 B2 * | 12/2002 | Matsumoto et al. ........ 378/154 |

FOREIGN PATENT DOCUMENTS

| JP | 55-012429 | 1/1980 |
| JP | 56-11395 | 2/1981 |

* cited by examiner

*Primary Examiner*—Craig E. Church
*Assistant Examiner*—Hoon Song
(74) *Attorney, Agent, or Firm*—Fitzpatrick, Cella, Harper and Scinto

(57) ABSTRACT

An X-ray image photographing apparatus includes an image obtaining portion for obtaining an X-ray distribution transmitted through an object, a grid detecting system having a construction for obtaining information from a grid side by the action of inserting the grid for decreasing scattered rays into the apparatus, and detecting at least one of the presence or absence of the grid, the kind of the grid and the presence or absence of the replacement of the grid by the use of the construction, an image processing system for image processing and outputting image data collected by the image obtaining portion, and a memory portion preserving therein a plurality of sets of image processing parameters for controlling the image processing system. The image processing system selects the image processing parameters preserved in the memory on the basis of at least the result of the detection by the grid detecting system and executes image processing.

7 Claims, 7 Drawing Sheets

X-RAY IMAGE PHOTOGRAPHING APPARATUS AND GRID DEVICE

This is a continuation-in-part application of U.S. patent application Ser. No. 09/392,617 filed on Sep. 9, 1999 now U.S. Pat. No. 6,501,829.

BACKGROUND OF THE INVENTION

1. Field of the Invention

This invention relates to an X-ray image photographing apparatus for effecting photographing by the use of a grid, and a grid device.

2. Related Background Art

When radiation such as X-ray, α-ray, β-ray, γ-ray, an electron beam or an ultraviolet ray is applied to a certain kind of fluorescent material, part of this radiation energy is accumulated in the fluorescent material. It is known that excitation light such as visible light may be applied to this fluorescent material, whereby the fluorescent material exhibits accelerated light emission in conformity with the accumulated energy. The fluorescent material exhibiting such a nature is called an accumulative fluorescent material or an accelerative fluorescent material.

Heretofore, by the utilization of this accumulative fluorescent material, the radiation image information of an object such as a human body has been once recorded on a sheet of accumulative fluorescent material, and this sheet of accumulative fluorescent material has been scanned by the use of excitation light such as a laser beam to thereby emit accelerated light, and the obtained accelerated light has been read to thereby obtain an image signal. A radiation image information recording-reproducing system for outputting the radiation image of the object as a visible image to a recording material such as a photosensitive material or a display apparatus such as a CRT on the basis of this image signal is proposed, for example, by Japanese Patent Application Laid-Open No. 55-12429, Japanese Patent Application Laid-Open No. 56-11395, etc.

Also, in recent years, an apparatus using a semiconductor sensor to likewise photograph an X-ray image has been developed. These systems, as compared with a conventional radiation photographic system using silver salt photographs, have the practical advantage that an image can be recorded over a very wide range of radiation exposure area. That is, X-rays in a very wide dynamic range are read by photoelectric converting means and converted into an electrical signal. By the use of this electrical signal, the radiation image is outputted as a visible image to the recording material such as a photosensitive material or the display apparatus such as a CRT, whereby there can be obtained a radiation image which is not affected by the fluctuation of a radiation exposure amount.

However, in the analog photographing using the accumulative fluorescent material shown in the above-described example of the prior art, use is made of various grids for decreasing scattered rays during photographing, but in digital photographing using a semiconductor sensor, moiré fringes are created from the relation between the sampling pitch and the frequency of the grid, and in an apparatus, a plurality of kinds of grids or an image by without a grid is not supported.

SUMMARY OF THE INVENTION

The present invention has been made in consideration of the above situation, and has as its object to improve operability and radiographing efficiency by automatically making setups required for radiographing operations and processing of radiographs.

It is an object of the present invention to solve the above-noted problem and to provide an X-ray image photographing apparatus which can execute appropriate photographing or image processing by a plurality of kinds of grids or by without a grid and a grid device suitable therefor.

It is an another object of the present invention to provide a radiographic apparatus which can execute appropriate radiographing or image processing in accordance with information concerning a grid, and a radiographic apparatus and a grid device suitable therefor.

It is a still another object of the present invention to provide a radiographic apparatus which can execute appropriate radiographing or image processing in accordance with information concerning a grid and a pixel density of an image obtaining portion, and a radiographic apparatus and a grid device suitable therefor.

According to the present invention, the foregoing object is attained by providing an X-ray image photographing apparatus which has:

a photographing portion having an image obtaining portion for obtaining a distribution of X-ray having transmitted through an object, and can mount a grid unit including at least a grid for removing scattered rays from the object;

a grid detection system for obtaining information from said grid unit or by using said grid unit, and detecting at least one of presence or absence of the grid, a kind of the grid and presence or absence of replacement of the grid; and a control portion for executing photographing or image processing on the basis of at least the result of the detection by said grid detection system.

According to the present invention, the foregoing object is also attained by providing an X-ray image photographing apparatus which has:

a photographing portion having an image obtaining portion for obtaining a distribution of X-ray having transmitted through an object, and can mount a grid unit including at least a grid for removing scattered rays from the object;

a grid detection system for obtaining information from said grid unit or by using said grid unit, and detecting at least one of presence or absence of the grid, a kind of the grid and presence or absence of replacement of the grid;

a control portion for executing photographing or image processing on the basis of at least the result of the detection by said grid detection system; and an inputting portion by which photographing information as to which portion of the object is photographed is input;

wherein said control portion having a judging portion for judging the propriety of the adaptation of the grid on the basis of at least the photographing information input by said inputting portion and the result of the detection by said grid detection system.

Further, the foregoing object is also attained by providing an X-ray image photographing apparatus which has:

sensor means for obtaining a distribution of X-ray having transmitted through an object;

housing means for housing said sensor means, and can mount a grid unit including at least a grid for removing scattered rays from the object;

grid detecting means for obtaining information from said grid unit or by using said grid unit to thereby detect at least one of presence or absence of the grid, a kind of the grid and presence or absence of replacement of the grid; and control means for executing photographing or image processing on the basis of at least the result of the detection by said grid detection means.

Furthermore, the foregoing object is also attained by providing a grid device which is used for an X-ray image photographing apparatus and which has:

a grid;

a frame holding said grid; and information providing means provided on said frame, said information providing means being designated to provide information concerning at least one of presence or absence of the grid, a kind of the grid and presence or absence of replacement of the grid to said X-ray image photographing apparatus.

Further, the foregoing object is also attained by providing an X-ray image photographing apparatus which has:

a photographing portion having an image obtaining portion for obtaining a distribution of X-ray having transmitted through an object, and can mount a grid unit including at least a grid for removing scattered rays from the object;

a grid detection system detecting at least one of presence or absence of the grid, a kind of the grid and presence or absence of replacement of the grid; and an image processing system for determining an image processing parameter concerning at least one of gain correction, frequency processing, contrast processing and image compression on the basis of at least the result of the detection by said grid detection system for image data obtained by said image obtaining portion and executing image processing.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object;

a grid detection portion for obtaining information from said grid unit or by using said grid unit, and detecting information concerning the grid; and a control portion for executing radiographing or image processing on the basis of at least the result of the detection by said grid detection portion.

Further, the foregoing object is also attained by providing a grid device for use in a radiographic apparatus which comprises:

a grid;

a frame holding said grid; and information providing portion provided on said frame, said information providing portion being designed to provide information concerning the grid to said radiographic apparatus.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object;

a grid detection portion detecting information concerning the grid; and an image processing portion for determining an image processing parameter concerning at least one of gain correction, frequency processing, contrast processing and image compression on the basis of at least the result of the detection by said grid detection portion for image data obtained by said image obtaining portion and executing image processing.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object; and a grid detection portion for obtaining information from said grid unit or by using said grid unit, and detecting information concerning the grid.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object;

a grid detection portion for obtaining information from said grid unit or by using said grid unit, and detecting information concerning the grid;

a pixel density detection portion for detecting information concerning a pixel density of said image obtaining portion; and a control portion for executing radiographing or image processing on the basis of at least the results of the detection by said grid detection portion and said pixel density detection portion.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object;

a grid detection portion detecting information concerning the grid;

a pixel density detection portion for detecting information concerning a pixel density of said image obtaining portion; and an image processing portion for determining an image processing parameter concerning at least one of gain correction, grid erasing processing, frequency processing, contrast processing and image compression on the basis of at least the results of the detection by said grid detection portion and said pixel density detection portion for image data obtained by said image obtaining portion and executing image processing.

Further, the foregoing object is also attained by providing a radiographic apparatus which comprises:

a radiographing portion having an image obtaining portion for obtaining a distribution of X-ray having transmitted through an object, and can mount a grid unit including at least a grid for removing scattered rays from the object;

a grid detection portion for obtaining information from said grid unit or by using said grid unit, and detecting information concerning the grid; and a pixel density indication portion for indicating information concerning a pixel density of said image obtaining portion to an external apparatus.

Other features and advantages of the present invention will be apparent from the following descriptions taken in conjunction with the accompanying drawings, in which like reference characters designate the same or similar parts throughout the figures thereof.

DESCRIPTION OF THE PREFERRED EMBODIMENTS

Figure 1:
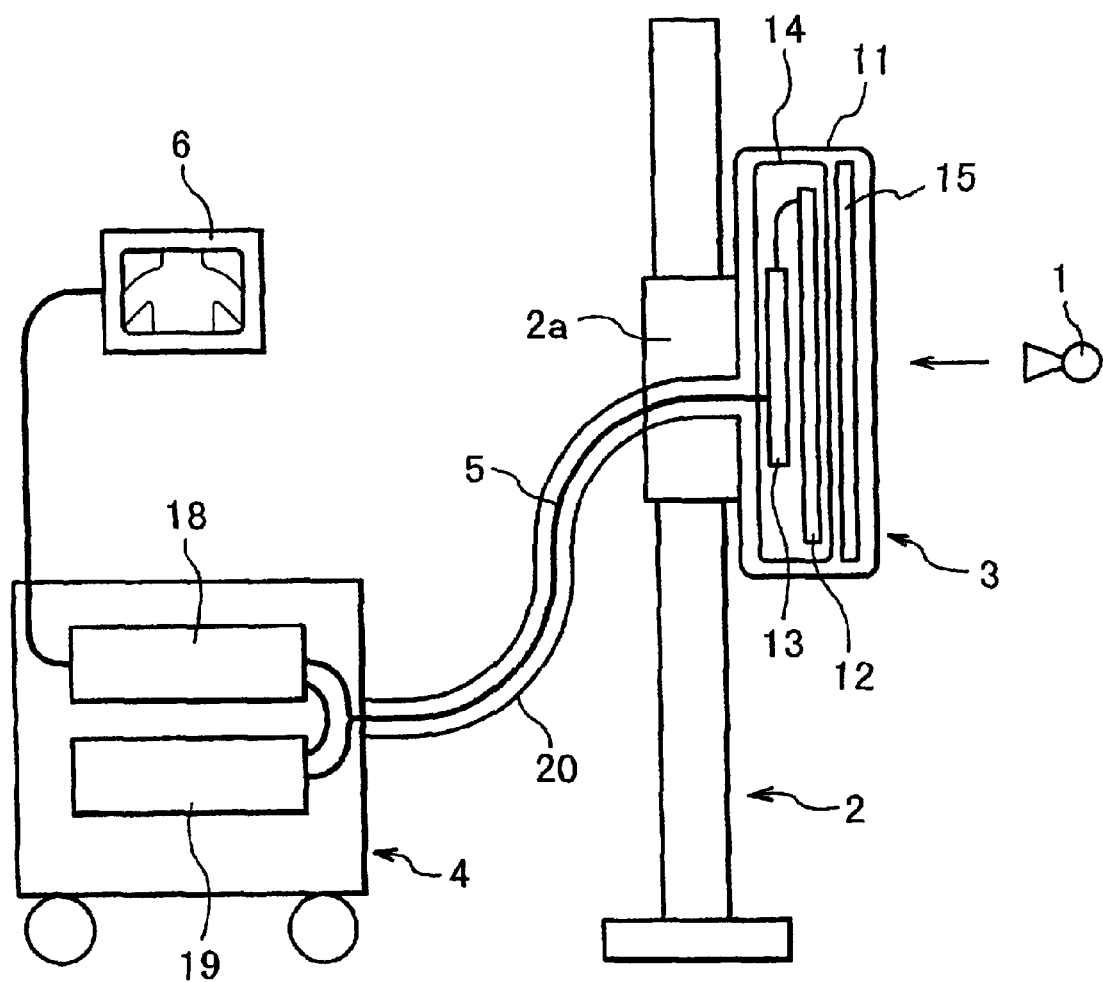
FIG. 1 is a schematic view of an embodiment of the present invention.

The present invention will hereinafter be described in detail with respect to an embodiment thereof shown in the drawings.

Figure 2:
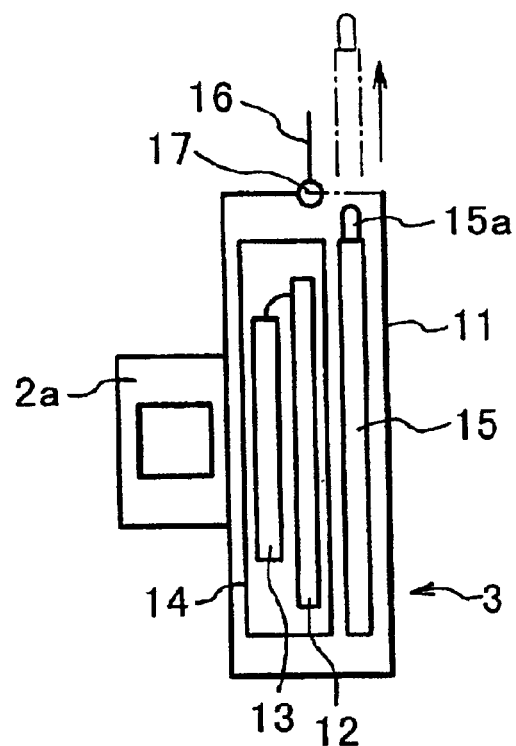
FIG. 2 is a plan view of an X-ray photographing portion.

FIG. 1 is a schematic view of an X-ray digital image photographing apparatus, and FIG. 2 is a plan view of the X-ray photographing apparatus. The X-ray digital image photographing apparatus is comprised of an X-ray generating portion 1 a stand 2, an X-ray photographing portion 3, a control portion 4 for controlling the X-ray photographing portion 3, a cable 5 for connecting the X-ray photographing portion 3 and the control portion 4 together, and a monitor 6 for displaying a signal processed in the control portion 4.

Also, the X-ray photographing portion 3 is vertically movable through the movable portion 2a of the stand 2, and can freely change its height in accordance with the position of an object by this vertical movement, and is designed to be capable of photographing the predetermined position of the object located between the X-ray photographing portion 3 and the X-ray generating portion 1.

An X-ray image receiving portion 14 comprising a radiation image detector 12 and a reading circuit 13 for reading out a signal from this radiation image detector 12, and a grid unit 15 including a grid for removing the scattered rays of the object are contained in the housing 11 of the X-ray photographing portion 3. Also, a handle 15a is provided on a side of the grid unit 15. Further, an openable-closable cover 16 is mounted on a side of the X-ray photographing portion 3 through a hinge 17.

The grid unit 15 and the X-ray image receiving portion 14 are disposed in parallel in the housing 11 of the X-ray photographing portion 3, and the grid unit 15 can be taken out of the X-ray photographing portion 3 by opening the cover 16 and pulling the handle 15a.

The control portion 4 is comprised of an image processing portion 18 for effecting a filtering process such as a reduction in the noise or edge emphasis of an image digital signal supplied from a memory circuit 13, and a power source portion 19 for supplying a power source to the X-ray image receiving portion 14 and the image processing portion 18. The connection between the X-ray photographing portion 3 and the control portion 4 is made by the cable 5 comprising a signal line and a power source line, and this cable 5 is covered and protected by a flexible tube 20. The flexible tube 20 is of a flexible material and therefore can follow the vertical movement of the X-ray photographing portion 3.

In an X-ray photographing apparatus system of such a construction, the X-ray photographing portion 3 is moved to a photographing position for a patient, and X-rays are applied from the X-ray generating portion 1 and photographing is effected. The image information of the object photographed by the X-ray photographing portion 3 is transmitted as a digital signal to the image processing portion 18 by the cable 5, and various image processings are effected in conformity with the presence or absence of the use and kind of the grid.

Figure 3:
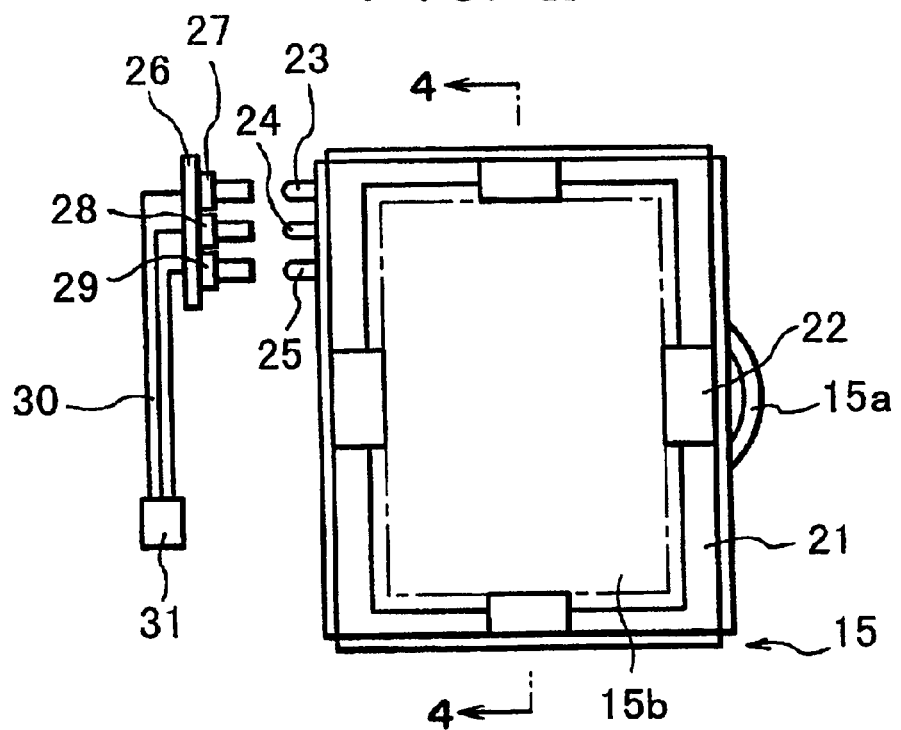
FIG. 3 is a front view of a grid.
Figure 4:
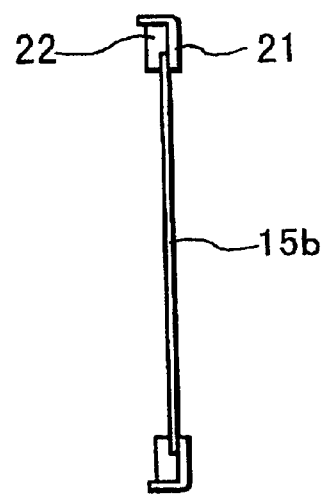
FIG. 4 is a cross-sectional view taken along the line 4—4 of FIG. 3.

FIG. 3 is a front view of a grid unit 15, and FIG. 4 is a cross-sectional view taken along the line 4—4 of FIG. 3. The grid unit 15 is comprised of a handle 15a, a grid body 15b and a grid holding portion 21, the grid body 15b mounted in the X-ray photographing portion 3 is fixed to the frame-like grid holding portion 21 through a fixing member 22, and the grid holding portion 21 has its four sides bent at right angles to improve the strength thereof. Of these four bent sides, convex projections 23, 24 and 25 are equidistantly formed on the end portion of the side of the surface opposed to the handle 15a. Also, a switch mounting plate 26 is provided in the X-ray photographing portion 3, and microswitches 27, 28 and 29 are provided on this switch mounting plate 26 so as to be opposed to the projections 23, 24 and 25, respectively, and a grid discriminating circuit 31 is connected to the microswitches 27, 28 and 29 through a lead wire 30.

The microswitch 27 is disposed so as to be changed from its OFF state to its ON state by the projection 23 provided on the grid holding portion 21 when the grid unit 15 is mounted on the X-ray photographing portion 3. Likewise, the microswitches 28 and 29 are adapted to be changed from their OFF state to their ON state by the projections 24 and 25, respectively. The ON and OFF states of the microswitches 27, 28 and 29 are transmitted to the grid discriminating circuit 31 by the lead wire 30, and the presence or absence of the grid body 15b and the kind of the grid body 15b are discriminated.

For example, it is conceivable to set so that if the microswitches 27, 28 and 29 are all in their ON state, it is discriminated that a grid body 15b of a first characteristic A is mounted, and if only the microswitch 27 is in its ON state, it is discriminated that a grid body 15b of a second characteristic B is mounted, and if all of the microswitches 27, 28 and 29 are in their OFF state, it is discriminated that the grid body 15b itself is not mounted.

Such setting is not restricted to this example, but various kinds of setting are possible depending on the combinations of the ON and OFF states of the microswitches 27, 28 and 29. The detecting means are not restricted to the microswitches 27, 28 and 29, but may also be lead switches utilizing a magnetic force or photoswitches utilizing a light, and the number of the detecting means can be selected as required.

Further, while in the above-described embodiment, description has been made of a case where the stationary grid body 15b is used, such a detecting method is applicable not only to a photographing apparatus using the stationary grid 15b, but also to a photographing apparatus which effects photographing with the grid body 15b moved relative to the X-ray image receiving portion 14 during photographing. For example, driving means such as a motor for moving the grid body 15b may be discretely provided in the X-ray photographing portion 3, and the grid body 15b is made movable relative to the grid holding portion 21, and during photographing, only the grid body 15b can be moved at a predetermined speed by the driving means.

In this case, as in the above-described embodiment, the detected means provided on the grid holding portion 21 can be intactly used, and the presence or absence of the grid or the characteristic of the grid body 15b can be discriminated independently of the movement of the grid body 15b.

Such detecting means is not directly provided on the grid body 15b, but is provided on the common grid holding portion 21 to thereby obtain the following advantages. Irrespective of the grid thickness depending on the grid ratio, the grid inserting portion in the photographing apparatus can be simplified into the same shape, and in the case of photographing in which the grid is moved, the ON and OFF of the microswitches are not repeated each time the grid is moved and therefore, the durability of the apparatus is improved. Also, the grid can be protected when the grid is detached from the photographing apparatus. Further, if design is made such that the presence of the grid body 15b in the X-ray photographing portion 3 is detected and the grid driving means is operated only in the case of photographing in which the grid is moved, the grid driving means can be prevented from being driven by mistake when the grid body 15b is not mounted in the X-ray photographing portion 3 and when photographing is effected with the grid fixed.

Also, it will be unnecessary to provide new grid detecting means if design is made such that the grid detecting microswitches 27, 28 and 29 as described above are not used, but a parameter amount fluctuated by a load applied to the motor when only the grid driving means, e.g. the motor is operated before photographing, or during photographing is detected to thereby discriminate the presence or absence or the weight of the grid body 15b. Specifically, for example, the current value flowing to the motor when the motor is operated is defined as a parameter amount, and the current value when this current value has assumed a balanced state and a preset discrimination current value can be compared with each other to thereby discriminate the presence or absence of the grid body 15b and the characteristic of the grid body 15b which depends on the weight of the grid body 15b. Chiefly the amount of lead in the grid body 15b, i.e., the grid density, is conceivable as the characteristic of the grid body 15b which depends on the weight of the grid body 15b.

Figure 5:
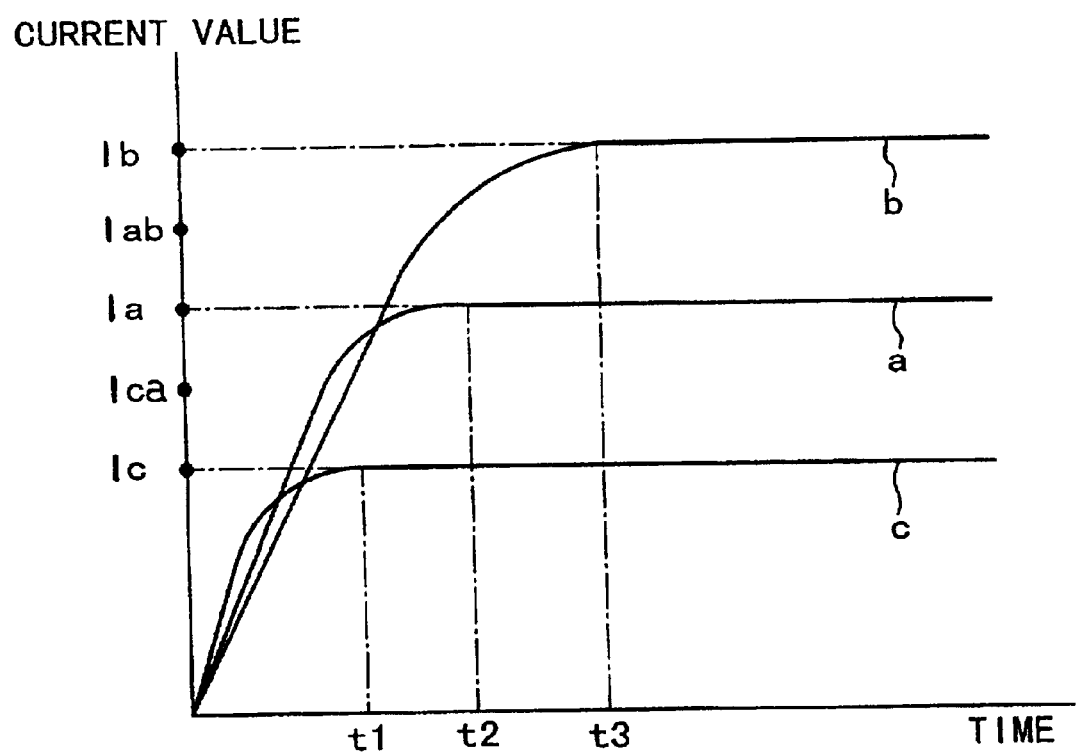
FIG. 5 is a graph of a current value flowing to a motor on the basis of a lapse time.

FIG. 5 is a graph showing the current value flowing to the motor to the lapse time. When the grid body 15b is not present in the X-ray photographing portion 3, the load torque applied to the motor is minute and therefore, the current value from the start of the rotation of the motor changes as indicated by a curve C, and the current balance value converges to Ic after a current balance reaching time t1. Likewise, the current values when grids A and B are mounted become as indicated by curves a and b, respectively, and after current balance reaching times t2 and t3, the current values become Ia and Ib, respectively. The grid B is higher in grid density and greater in weight than the grid A and therefore, the load torque thereof becomes great, and the current values become Ib>Ia>Ic. Also, the increase rate of the current value during the rising of the rotation of the motor is great in the order of curves b, a and c, and the current balance reaching time becomes long in the order of t3>t2>t1.

Here, when discrimination current values Ica and Iab are preset so as to be Ib>Iab>Ia>Ic, it becomes known that if the current value i after the current balance reaching time t3 is Ica>i, no grid is mounted, and if Tab>i>Ica and i>Iab, the grids A and B are mounted respectively, and the discrimination of the presence or absence and the kind of the grid becomes possible. In the present embodiment, the parameter amount fluctuated by the load applied to the grid driving means is defined as the current value i in the balanced state, but may be defined as the increase rate of the current value or the required time until the balanced state is reached, and use may be made of the number of rotations of the motor inversely proportional to the load torque to obtain a similar effect.

Figure 6:
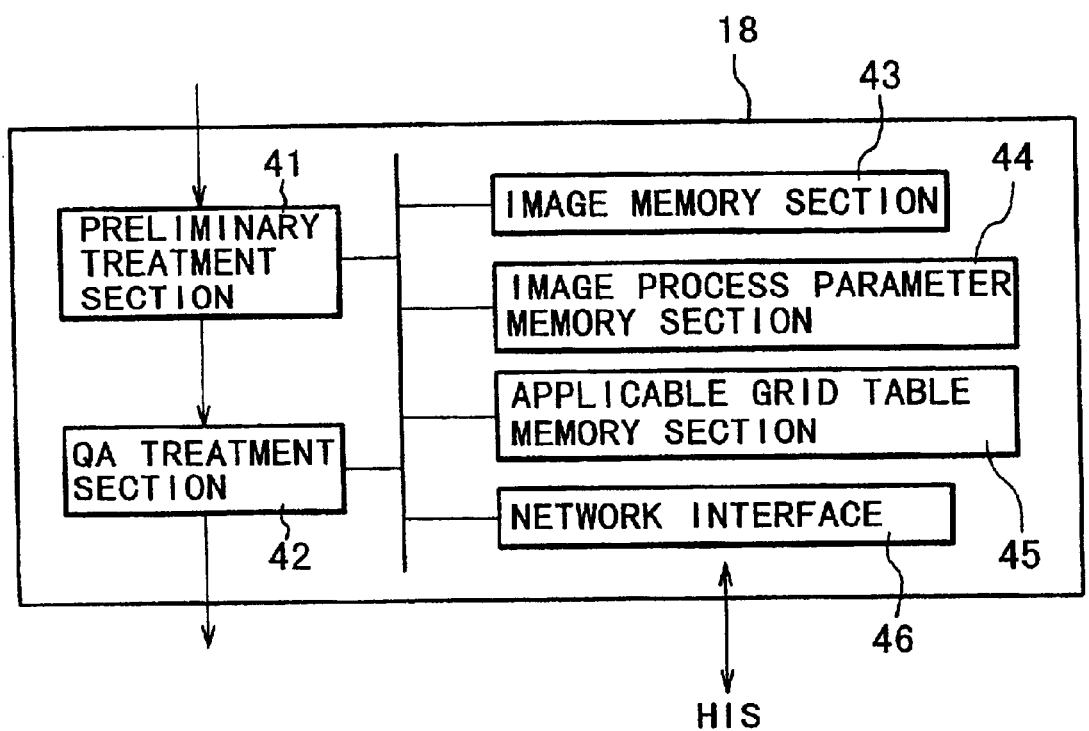
FIG. 6 is a block circuit diagram of an image processing portion.

FIG. 6 shows a block circuit diagram of the image processing portion 18, which can select appropriate image processing by the utilization of the information of the presence or absence and the kind of the grid body 15b obtained by the method as described above. The image processing portion 18 is comprised of a preliminary treatment section 41, a QA treatment section 42, an image memory section 43, an image process parameter memory section 44, an applicable grid table memory section 45 and a network interface 46. Gain correction, offset treatment, LOG conversion and grid erasing process, not shown, are carried out in the preliminary treatment section 41.

In the photographing in a fixed grid system, gain images are all photographed without the use of a grid. That is, in the fixed grid system, irrespectively of the presence or absence and the kind of the grid, the grid is not used but a photographed gain image W1 is used. Also, in the photographing in a movable grid system, gain images W2–W4 collected by the grid used in the photographing are used. One of the reasons for this is that energy characteristic differs from grid to grid and therefore gain images similar in the quality of lines to each other are used.

Again in the case of the movable grid system, when no grid is mounted, a gain image using no grid is used for correction. However, there is no possibility of shading occurring even if the gain image is not changed over by a grid and therefore, the quality of image will not be greatly affected even if the gain image is not changed over.

Such gain images W1–W4 are preserved in the image memory section 43, and by the control of the preliminary treatment section 41, an image process parameter table shown in Table 1 below which is preserved in the image process parameter memory section 44 is referred to from the result of the detection by the grid detecting means, and a corresponding gain image is down-loaded from the image memory section 43.

TABLE 1

| Grid | gain image | grid erasing process | Frequency emphasizing process | harmony processing |
|---|---|---|---|---|
| no grid | W1 | absent | Absent | gamma 4.4 |
| Grid A | W2 | present, frequency Fa | present, Frequency F1 | gamma 4.0 |
| Grid B | W3 | present, | present, | gamma 4.0 |

TABLE 1-continued

| Grid | gain image | grid erasing process | Frequency emphasizing process | harmony processing |
|------|------------|----------------------|-------------------------------|--------------------|
| grid C | W4 | frequency Fb present, frequency Fc | frequency F2 present, frequency F3 | gamma 4.0 |

Likewise, the parameter of the grid erasing process is controlled by the presence or absence of the grid and the kind of the grid. The grid erasing process is carried out only in the case of the fixed grid system, and is not used in the case of the movable grid system. The advantage of the photographing by the fixed grid system is that high-speed photographing is possible, while on the other hand, the fringes of the grid are actualized in the image, and this is disliked as hindering diagnosis by some doctors. So, the erasing process of erasing the grid present in the image by image processing is carried out.

If the sampling frequency Fs of a sensor system is determined, in which frequency the fringes are created when which grid is used can be found by calculation. When the frequency of the grid is defined as Fg, if Fs>Fg, fringes are formed in the frequency Fg and therefore, they are removed by filter processing. As regards the frequency of the band cut filter at this time, the kind of the grid is detected, whereby the cut frequency Fa in the image process parameter table preserved in the image process parameter memory section 44 is determined.

Also, if Fs<Fg, the fringes of moiré are created in Fs−(Fg−Fs)=2Fs−Fg. As in this case, the frequency of this 2Fs−Fg is referred to from the image process parameter table by the band cut filter and a filter is constituted.

As regards also the frequency process which is one of QA processes, the parameter is adjusted by the grid. Here, the purposes are that in the grid processing, a frequency area weakened as a side effect is restored to its original state and that the grid which is not completely erased is not emphasized, but other frequency bands effective for diagnosis are emphasized.

These filter parameters are also determined by searching for the image process parameter table on the basis of the grid information from the detecting means.

Finally, harmony processing is carried out, but generally in photographing which does not use a grid, although somewhat, the contrast of the entire image is reduced by scattered rays. In order to correct this, it is desirable to increase and convert the contrast in the harmony processing.

The process in which the parameter is changed depending on the presence or absence and the kind of the grid has been disclosed regarding the processing shown in Table 1, whereas the processing related to the grid is not restricted thereto, but also in image compression regarding the post-processing of a diagnosed image, it is conceivable for the parameter to be adjusted so as not to emphasized the grid. It is nor restricted to an adjusting method for the processed parameter utilizing grid information, but is determined by the desire of a doctor or an engineer.

Figure 7:
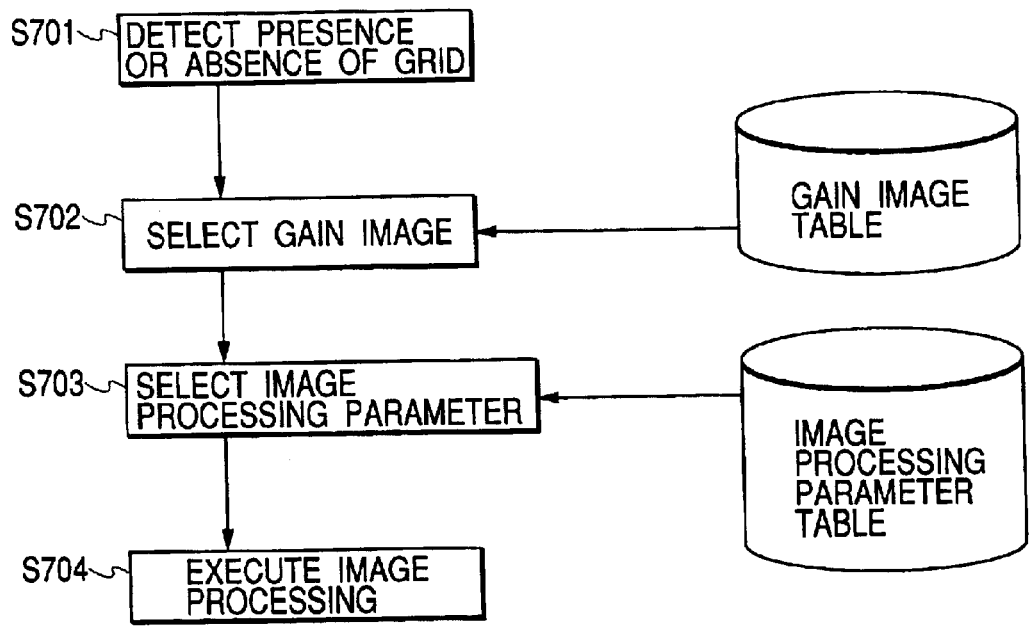
FIG. 7 is a diagram for illustrating the image processing flow executed by an image processing portion 18.

The image processing flow when image processing is carried out on the basis of the information about the presence or absence of the grid or the information about the kind of the grid described above will now be descried with reference to FIGS. 7 and 8. FIG. 7 illustrates the image processing flow by the image processing portion 18 based on the result of the detection when the grid discriminating circuit 31 detects only the presence or absence of the grid. First, the image processing portion 18 receives the information about the presence or absence of the grid discriminated by the grid discriminating circuit 31 (step S701). Next, the image processing portion 18 selects a gain image from a gain image table on the basis of the information about the presence or absence of the grid (step S702). When a fixed grid system is used, the gain image read out from the gain image table is the same irrespective of the presence or absence of the grid, as described above. That is, the gain image acquired without the use of the grid in advance is selected. When a movable grid system is used radiation quality (the energy of X-rays) differs depending on the presence or absence of the grid as described above and therefore, different gain images are selected in conformity with the presence or absence of the grid. Subsequently, the image processing portion 18 selects another image processing parameter on the basis of the information about the presence or absence of the grid (step S703). Image processing parameters include, for example, parameters for the grid erasing processing, the frequency emphasizing processing, the gradation or contrast processing, etc. as shown in Table 1 above. For example, whether the grid erasing processing should be carried out is selected on the basis of at least the information about the presence or absence of the grid. There is also a case where the parameter of the frequency emphasizing processing such as a sharpening processing is selected in accordance with the presence or absence of the grid erasing processing. Also, the parameter (e.g. gamma) of the gradation processing is selected on the basis of at least the information about the presence or absence of the grid. The image processing portion 18 executes image processing on the basis of the parameters selected in the manner described above (step S704).

Figure 8:
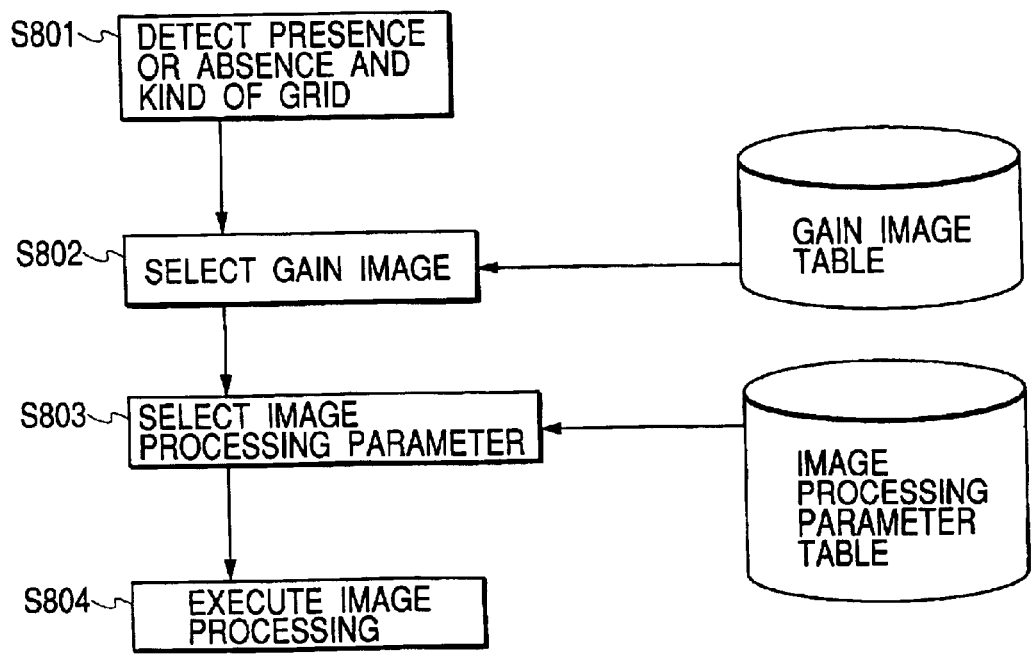
FIG. 8 is a diagram for illustrating the image processing flow executed by the image processing portion 18.

FIG. 8 illustrates the image processing flow executed by the image processing portion 18 based on the result of the detection when the grid discriminating circuit 31 detects not only the information about the presence or absence of the grid but also the information about the kind of the grid. First, the image processing portion 18 receives the information about the presence or absence and a kind of the grid discriminated by the grid discriminating circuit 31 (step S801). Next, the image processing portion 18 selects a gain image from the gain image table on the basis of the information about the presence or absence and a kind of the grid (step S802). When the fixed grid system is used, the gain image read out from the gain image table is the same irrespective of the presence or absence of the grid, as described above. That is, the gain image acquired without the use of the grid in advance is selected. When the movable grid system is used, radiation quality (the energy of X-rays) differs depending on the presence or absence and a kind of the grid as described above and therefore, different gain images are selected in conformity with the presence or absence and a kind of the grid. Subsequently, the image processing portion 18 selects another image processing parameter on the basis of the information about the presence or absence and kind of the grid (step S803). The image processing parameters include, for example, parameters for the grid erasing processing, the frequency emphasizing processing, the gradation or contrast processing, etc. as shown in Table 1 above. For example, whether the grid erasing processing should be carried out is selected on the basis of at least the information about the presence or absence of the grid. Also, other parameter of the grid erasing processing (for example, the frequency characteristic of the aforedescribed band cut filter or the like) is selected on the basis of at least the information about the kind of the grid. There may also be a case where the parameter of the frequency emphasizing processing such as the sharpening processing is selected in conformity with the presence or absence of the grid erasing processing and other parameters. Further, the amount of scattered radiation changes in conformity with the kind of the grid and as the result, the contrast of minute structure may sometimes change, and in such a case, the parameter of the frequency emphasizing processing is selected on the basis of at least the information about the presence or absence and a kind of the grid. Also, the parameter (e.g. gamma) of the gradation processing is selected on the basis of at least the information about the presence or absence and a kind of the grid. The image processing portion 18 executes image processing on the basis of the parameters selected in the manner described above (step S804).

In the foregoing, description has been made of the fact that the image processing parameter is adjusted by the information regarding the presence or absence or the kind of the grid, but changing the grid depending on the photographing method means that an appropriate grid is determined by the photographing method. In the image photographing apparatus of the present embodiment, before the photographing by the application of X-rays, the inputting of the photographing method as to what region is to be photographed with what intention is effected from a hospital information system HIS or a radiation information systems RIS by way of an input portion belonging to the display apparatus 17 or a network interface 46.

For example, suppose a case where if as shown in Table 2 below, the region to be photographed is the front of the breast, the use of the grid A is appropriate and if the region to be photographed is a limb, not using the grid is appropriate.

TABLE 2

| Photographing method | grid |
| --- | --- |
| breast image | grid A |
| thoracic vertebrae image | grid B |
| limb image | no grid |
| head image | grid C |

In the present embodiment, the kind of an appropriate grid retrieved from the photographing method and the kind of the grid detected by the grid detecting means are compared with each other, and if the selected grid is not appropriate, the display apparatus 17 can be given the function of displaying it. The photographing method shown in Table 2 and the corresponding table of the grid are preset and can be preserved in the applicable grid table memory section 45.

While in the above description, it is premised to have the means for detecting the characteristic of the grid, and in FIG. 3, there are shown the construction of the grid unit 15 and a method of discriminating between the presence and absence of the grid in the photographing apparatus and a grid of what characteristic is mounted, the mechanism can also be simplified as a construction having only the means for detecting the presence or absence of the grid.

In this case, the determination as to a grid of what characteristic is mounted is effected by the use of discrete means. For example, there is adopted a construction in which the deviation of the present or absent state of the grid detected by grid presence or absence detecting means is monitored and whether the grid has been changed is detected by the presence or absence of a state in which the grid is absent, and when there is the replacement of the grid, a panel for requiring idle exposure for the selection of the kind of the grid is displayed on the display portion 12.

This idle exposure is photographed in a state in which there is no object and moreover, with the grid fixed. This fixed grid idle exposure image is analyzed by an image analyzing portion, not shown, provided discretely from the image processing portion 18, whereby the determination of the kind of the grid is effected. Frequency analysis using Fourier conversion can be used as the image analyzing method, and specifically, at the position of spectrum, it is possible to determine the grid ratio by the period of the grid and the size of the spectrum. After grid judgment has been done by the use of such an image analyzing method, the result of the determination is used for the selection of the image processing parameter as previously described.

As described above, the X-ray image photographing apparatus according to each of the above-described embodiments can detect the presence or absence, kind, etc. of the grid, and the execution of appropriate photographing or image processing becomes possible, and the grid device can be suitably utilized therefor.

Embodiment 2

Figure 9:
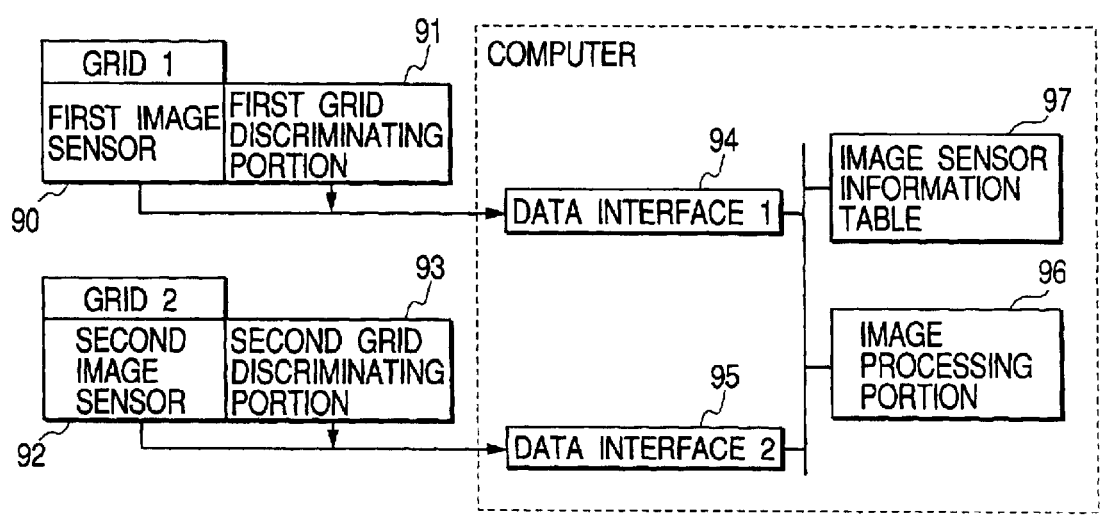
FIG. 9 is a schematic view of the image processing system of a second embodiment.

FIG. 9 shows the construction of Embodiment 2. This embodiment is an example of an image processing system constructed with a plurality of radiation image detectors (hereinafter referred to also as the image sensors) differing in resolution (the size or pitch of a pixel) being connected to one and the same image processing portion. In this case, it is necessary to change the parameter of image processing depending on the resolution of each radiation image detector. In FIG. 9, a first image sensor 90 and a second image sensor 92 are constructed so as to permit a grid detachably attached thereto, and are provided with a first grid discriminating portion 91 and a second grid discriminating portion 93, respectively. Each grid discriminating portion may be one for discriminating whether the grid is mounted, or one for discriminating not only the presence or absence of the grid, but also the kind of the grid based on the difference in the frequency, grid ratio or the like of the grid. When even the kind of the grid is to be discriminated, as described in Embodiment 1, a plurality of kinds of grids can be used and it becomes possible to select an image processing parameter conforming to the kind of the grid used.

An image processing portion 96 acquires information about resolution intrinsic to each image sensor by predetermined means. Therefore, each image sensor may desirably be comprised of an indicating unit for indicating the information to an external apparatus (image processing portion 96), for example, a transmitting unit for transmitting the information. For example, design can be made such that the information is forwarded from each image sensor to the image processing portion 96 through a data interface 94, 95 with image information, prior to the forwarding of the image information or at other timing. Alternatively, design may be made such that the image processing portion 96 can recognize the identification information (ID information) of each image sensor by similar or other means and also the image processing portion 96 can refer to an image sensor information table storing portion 97 storing therein the information about the resolution of each image sensor corresponding to the identification information as an image sensor information table. Typically, the table can be stored in computer-readable memory in or outside a computer to thereby manage the information about the characteristic of each image sensor. Also, design may be made such that the image processing portion 96 can acquire the information about the resolution of each image sensor by a contrivance similar to the system using the grid unit 15 and the grid discriminating circuit 31 in the previous embodiment. In the present embodiment, for simplicity, configuration is made such that the image sensor which has acquired image data is identified in conformity with which of the data interfaces 94 and 95 the image data has been acquired through. The image processing portion 96 obtains the information about the resolution of the identified image sensor from the image sensor information table, and determines the image processing parameter in conformity with the obtained information about the resolution, and executes image processing on the basis of the determined image processing parameter.

The flow of the processing executed by the image processing system of FIG. 9 will now be described with reference to FIG. 10. First, the acquisition of the image data is effected by the use of one of the image sensor 1 and the image sensor 2 (step S1001). The image processing portion 96 identifies the image sensor which has acquired the image data, depending on through which of the data interface 94 and the data interface 95 the image data has been acquired, and acquires the resolution of the identified image sensor by referring to a resolution table in the image sensor information table (step S1002). The information about the resolution is included in the aforedescribed image sensor information table. Next, the image processing portion 96 acquires the information about the presence or absence and/or a kind of the grid regarding the image sensor which has acquired the image data, by a technique similar to that in the previous embodiment (step S1003). The timing for the acquisition of this information is not restricted to that in the present embodiment, but can be before the image processing is executed, for example, immediately before the image processing or immediately before the acquisition of the image data. Then, the image processing portion 96 selects a gain image from a gain image table in conforming with the information about the presence or absence and/or a kind of the grid, under the same idea as that of the previous embodiment (step S1004). However, in the selection of the gain image in the present embodiment, in addition to the information about the presence or absence and/or a kind of the grid, the identification information of the image sensor which has acquired the image data is used. When the image sensor is variable in the resolution (pixel density) thereof, the information about the resolution is also used in the selection of the gain image.

Next, the image processing portion 96 selects an image processing parameter from an image processing parameter table (step S1005). This selection is also effected under an idea similar to that of the previous embodiment, but the present embodiment differs from the previous embodiment in that in addition to the information about the presence or absence and/or a kind of the grid, the information about the resolution of the image sensor is used to select the image processing parameter. The parameter of default prepared in advance is stored in the image processing parameter table and from this table, an image processing parameter conforming to the information about the presence or absence and/or a kind of the grid and the information about the resolution of the image sensor is selected. The image processing parameter stored in this table is the parameter of default and during image processing, the user can change it depending on individual situations (the characteristic of an object to be radiographed, etc.).

The necessity of adjusting the image processing parameter in conformity with the resolution of the image sensor will now be described by taking an example. For example, when spatial frequency processing (such as an image sharpening processing effected during QA processing) is to be effected by the use of a filter of a mask size of 7×7 pixels, if the pixel size (pixel density) of image data applied differs, the spatial frequency characteristic of the aforementioned filter of 7×7 pixels will also differ. However, when a clinical image is supposed, for example, a spatial frequency forming the edge of a blood vessel at a predetermined region in the human body is approximately constant and therefore, if the purpose of image processing is to make the blood vessel easy to observe (emphasize), it is desirable to make the frequency characteristic of the spatial filter approximately constant independently of the resolution (pixel density) of the image sensor. Consequently, to effect filter processing having an approximately equal frequency characteristic to images differing in resolution, it is necessary to use a filter having a coefficient and/or a mask size conforming to the resolution (pixel density) of the image sensor. Consequently, in the present embodiment, the image processing parameter is selected in conformity with the information about the presence or absence and/or a kind of the grid and the information about the resolution of the image sensor.

Also in the grid erasing processing, the adjustment of the parameter depending on the resolution of the image sensor becomes necessary. For example, when the Nyquist frequency of the image sensor is defined as Fn and the frequency of the grid is defined as Fg, if Fg≦Fn, a stripe-shaped pattern (fringes due to the grid) of the spatial frequency Fg appears on the image, and if Fg>Fn, a stripe-shaped pattern of the spatial frequency (2Fn−Fg) appears on the image. Accordingly, when the grid erasing processing is carried out, the image processing portion 96 calculates or selects the frequency (Fg or 2Fn−Fg) of the stripes attributable to the grid on the basis of the information about the presence or absence and/or a kind of the grid and the information about resolution of the image sensor.

There is a case where a frequency of the grid suited for use exists depending on the characteristic of the image sensor. A grid frequency suitable for each image sensor is theoretically or experimentally determined. According to our experiment, a grid of about 40lP/cm is suitable for an image sensor of a pixel pitch of 160 micron, and a grid of about 60lP/cm is suitable for an image sensor of a pixel pitch of 100 micron (here, 1p means a line pair). In this case, in an image acquired by each image sensor, each grid forms a different frequency spectrum. In the grid erasing processing, use is made of a spatial filter for erasing a frequency component corresponding to this frequency spectrum. Consequently, again in this case, the image processing portion 96 calculates or selects the parameter of the grid erasing processing on the basis of the information about the presence or absence and/or a kind of the grid and the information about the resolution of the image sensor. Here, when the grid is not mounted on the grid unit ("no" grid is discriminated by the grid discriminating circuit 31), the parameter of the grid erasing processing is "no", that is, the grid erasing processing is not executed.

Also, under a similar idea as that of the previous embodiment, the image processing portion 96 selects the parameter (e.g. gamma) of gradation processing and the parameter of image compression on the basis of the information about the presence or absence and/or a kind of the grid and the information about the resolution of the image sensor.

The processing parameters adjusted in conformity with the information about the presence or absence and/or a kind of the grid and the information about the resolution of the image sensor and the adjusting technique therefor are not restricted to those described above, but rather various changes are possible and they are usually determined on the basis of the desire of a medical doctor or a technician.

The image processing portion 96 executes image processing on the basis of the parameters selected in the manner described above (step S1006).

Other Embodiment

Note that the present invention may be applied to either a system constituted by a plurality of apparatuses (e.g., image processing apparatuses, interfaces, radiographic apparatuses, X-ray generation apparatuses, and the like) or an arrangement that integrates an image processing apparatus and a radiographic apparatus, or the like.

Further, the object of the present invention can also be achieved by providing a storage medium storing program codes for performing the aforesaid processes to a computer system or apparatus (e.g., a personal computer), reading the program codes, by a CPU, MPU or the like of the computer system or apparatus, from the storage medium, then executing the program.

In this case, the program codes read from the storage medium realize the functions according to the embodiments, and the storage medium storing the program codes constitutes the invention.

Further, as the storage medium, a floppy disk, a hard disk, an optical disk, a magneto-optical disk, CD-ROM, CD-R, a magnetic tape, a non-volatile type memory card, ROM or the like can be used for providing the program codes.

Furthermore, besides aforesaid functions according to the above embodiments are realized by executing the program codes which are read by a computer, the present invention includes a case where an OS (operating system) or the like working on the computer performs a part or entire processes in accordance with designations of the program codes and realizes functions according to the above embodiments.

Furthermore, the present invention also includes a case where, after the program codes read from the storage medium are written in a function expansion card which is inserted into the computer or in a memory provided in a function expansion unit which is connected to the computer, CPU or the like contained in the function expansion card or unit performs a part or entire process in accordance with designations of the program codes and realizes functions of the above embodiments.

Figure 10:
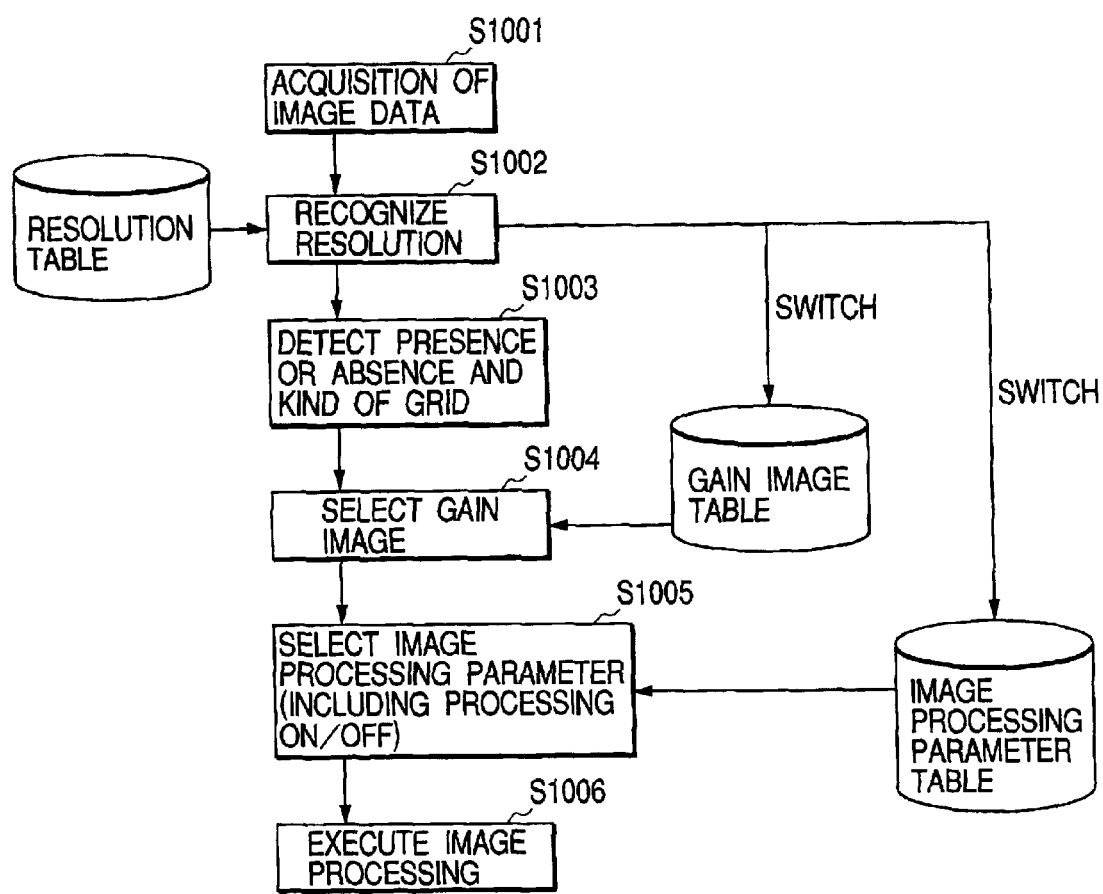
FIG. 10 is a diagram for illustrating the processing flow executed by the image processing system of FIG. 9.

In a case where the present invention is applied to the aforesaid storage medium, the storage medium stores program codes corresponding to the flowchart shown in FIG. 7, 8 or 10 described in the embodiments.

The present invention is not limited to the above embodiments and various changes and modifications can be made within the spirit and scope of the present invention. Therefore to apprise the public of the scope of the present invention, the following claims are made.

What is claimed is:

1. A radiographic apparatus comprising:
a radiographing portion having an image obtaining portion for obtaining a distribution of X-ray having been transmitted through an object, said radiographing portion being constructed to mount a grid unit including at least a grid for removing scattered rays from the object;
a grid detection portion for obtaining information from said grid unit or by using said grid unit, and detecting information concerning the grid;
a pixel density detection portion for detecting information concerning a pixel density of said image obtaining portion; and
a control portion for executing radiographing or image processing on the basis of at least the results of the detection by said grid detection portion and said pixel density detection portion.

2. A radiographic apparatus comprising:
a radiographing portion having an image obtaining portion for obtaining a distribution of X-ray having been transmitted through an object, said radiographing portion being constructed to mount a grid unit including at least a grid for removing scattered rays from the object;
a grid detection portion for detecting information concerning the grid;
a pixel density detection portion for detecting information concerning a pixel density of said image obtaining portion; and
an image processing portion for determining an image processing parameter concerning at least one of gain correction, grid erasing processing, frequency processing, contrast processing and image compression on the basis of at least the results of the detection by said grid detection portion and said pixel density detection portion for image data obtained by said image obtaining portion and executing image processing.

3. A radiographic apparatus comprising:
a radiographing portion having an image obtaining portion for obtaining a distribution of X-ray having been transmitted through an object, said radiographing portion being constructed to mount a grid unit including at least a grid for removing scattered rays from the object;
a grid detection portion for obtaining information from said grid unit or by using said grid unit, and detecting information concerning the grid;
a pixel density indication portion for indicating information concerning a pixel density of said image obtaining portion to an external apparatus; and
a control portion for executing radiographing or image processing on the basis of at least the results of the detection by said grid detection portion and said pixel density indication portion.

4. A radiographic apparatus comprising:
a sensor including a plurality of elements which convert radiation rays to data values corresponding to an image data;
a grid provided in front of said sensor, which is used for removing scattered rays caused from said radiation rays;
a determining unit which determines a state of said grid;
an obtaining unit which obtains an information relating to a pitch of said plurality of elements; and
an image processing unit which executes a predetermined process on said data values on the basis of a determination result of said determining unit and said information obtained by said obtaining unit.

5. A radiographic apparatus according to claim 4, wherein said grid is detachably attached to said apparatus, and said state of said grid includes a presence or an absence of said grid.

6. A radiographic apparatus according to claim 4, wherein said grid is exchangeable to said apparatus, and said state of said grid corresponds to a type of said grid.

7. A radiographic apparatus according to claim 4, wherein said predetermined process includes an image sharpening process for sharpening said data values corresponding to said image data, and a grid erasing process for removing a data value corresponding to an image of said grid from said data values corresponding to said image data.

UNITED STATES PATENT AND TRADEMARK OFFICE
CERTIFICATE OF CORRECTION

PATENT NO. : 6,850,597 B2
DATED : February 1, 2005
INVENTOR(S) : Kazuhiro Matsumoto et al.

It is certified that error appears in the above-identified patent and that said Letters Patent is hereby corrected as shown below:

Column 2,
Lines 24, 40 and 63, "X-ray having" should read -- X-ray having been --.
Line 55, "having" should read -- has --.

Column 3,
Lines 23, 41 and 64, "X-ray having" should read -- X-ray having been --.

Column 4,
Lines 13, 23, 40 and 61, "X-ray having" should read -- X-ray having been --.

Column 5,
Line 41, "1" should read -- 1, --.

Column 7,
Line 56, "to the lapse time." should read -- versus time elapsed. --.

Column 9,
Line 60, "emphasized" should read -- emphasize --.
Line 61, "is nor" should read -- is not --.
Line 67, "descried" should read -- described --.

Signed and Sealed this

Fourteenth Day of February, 2006

JON W. DUDAS
*Director of the United States Patent and Trademark Office*